(12) United States Patent
Petruno et al.

(10) Patent No.: US 8,024,148 B2
(45) Date of Patent: *Sep. 20, 2011

(54) END-OF-LIFE DISABLING OF A DIAGNOSTIC TEST SYSTEM

(75) Inventors: Patrick T. Petruno, San Jose, CA (US); Murray Lappe, Beverly Hills, CA (US)

(73) Assignee: Alverix, Inc., San Jose, CA (US)

( * ) Notice: Subject to any disclaimer, the term of this patent is extended or adjusted under 35 U.S.C. 154(b) by 652 days.

This patent is subject to a terminal disclaimer.

(21) Appl. No.: 11/625,786

(22) Filed: Jan. 22, 2007

(65) Prior Publication Data

US 2008/0028261 A1 Jan. 31, 2008

Related U.S. Application Data

(63) Continuation-in-part of application No. 11/312,951, filed on Dec. 19, 2005.

(51) Int. Cl.
*G06F 11/00* (2006.01)

(52) U.S. Cl. ............ 702/117; 702/22; 702/25; 422/68.1

(58) Field of Classification Search .................. 600/573; 436/524; 702/25; 422/68.1
See application file for complete search history.

(56) References Cited

U.S. PATENT DOCUMENTS

| | | | |
|---|---|---|---|
| 5,695,623 A * | 12/1997 | Michel et al. ............ 204/403.05 |
| 5,830,175 A | 11/1998 | Flower | |
| 5,837,546 A * | 11/1998 | Allen et al. ................... 436/169 |
| 5,861,256 A | 1/1999 | Glass et al. | |
| 6,136,610 A | 10/2000 | Polito et al. | |
| 6,268,162 B1 | 7/2001 | Phillips et al. | |
| 6,281,785 B1 | 8/2001 | Hamaguchi | |
| 6,377,894 B1 * | 4/2002 | Deweese et al. ................. 702/22 |
| 6,483,582 B2 | 11/2002 | Modlin et al. | |
| 6,629,057 B2 | 9/2003 | Zweig et al. | |
| 6,630,307 B2 | 10/2003 | Bruchez et al. | |
| 6,663,833 B1 | 12/2003 | Stave et al. | |
| 6,966,880 B2 | 11/2005 | Boecker et al. | |
| 2003/0119202 A1 | 6/2003 | Kaylor et al. | |
| 2003/0119203 A1 | 6/2003 | Wei et al. | |

(Continued)

OTHER PUBLICATIONS

TrueTrack Smart System® Blood Glucose Monitor, Owner's Manual, Home Diagnostics, Inc., pp. 1-33 (May 2006).

(Continued)

*Primary Examiner* — Drew A Dunn
*Assistant Examiner* — Hien Vo
(74) *Attorney, Agent, or Firm* — K&L Gates LLP

(57) ABSTRACT

Systems and methods for end-of-life disabling of a diagnostic test system are described. In one aspect, a diagnostic test system that includes a test unit and a disabling unit. The test unit performs at least one diagnostic test on a diagnostic assay to determine whether at least one analyte is present within a sample. The disabling unit determines a measure of current lifetime of the test unit and disables the test unit in response to a determination that the current lifetime measure meets an end-of-life threshold. In a diagnostic test method, at least one diagnostic test is performed on a diagnostic assay to determine whether at least one analyte is present within a sample. A measure of current lifetime of the test unit is determined. The test unit is disabled in response to a determination that the current lifetime measure meets an end-of-life threshold.

20 Claims, 4 Drawing Sheets

---

Perform At Least One Diagnostic Test On A Diagnostic Assay To Determine Whether At Least One Analyte Is Present Within A Sample — 26

Determine A Measure Of Current Lifetime Of The Test Unit — 27

Disable The Test Unit In Response To A Determination That The Current Lifetime Measure Meets An End-of-life Threshold — 28

U.S. PATENT DOCUMENTS

| | | |
|---|---|---|
| 2003/0171697 A1 | 9/2003 | Smith et al. |
| 2003/0175820 A1 | 9/2003 | Smith et al. |
| 2003/0207454 A1 | 11/2003 | Eyster et al. |
| 2004/0018637 A1 | 1/2004 | Polito et al. |
| 2004/0043502 A1 | 3/2004 | Song et al. |
| 2004/0151632 A1 | 8/2004 | Badley et al. |
| 2004/0214347 A1 | 10/2004 | LaBorde et al. |
| 2005/0033196 A1* | 2/2005 | Alroy .................... 600/573 |
| 2005/0221504 A1 | 10/2005 | Petruno et al. |
| 2005/0221505 A1 | 10/2005 | Petruno et al. |
| 2006/0014302 A1 | 1/2006 | Martinez et al. |
| 2006/0122782 A1 | 6/2006 | Petrilla et al. |
| 2006/0210435 A1 | 9/2006 | Alavie et al. |
| 2006/0216696 A1 | 9/2006 | Goguen |
| 2006/0240541 A1 | 10/2006 | Petruno et al. |
| 2006/0240568 A1 | 10/2006 | Petruno et al. |

OTHER PUBLICATIONS

Clearblue® Easy Digital Pregnancy Test, Inverness Medical Innovations, Inc., Product Description, http://www.clearblueeasy.com/our_products_digital_pregnancy_test.cfm, 2 pages (downloaded Nov. 16, 2006).

LidoSite™ Topical System, Brochure, B.Braun Medical Inc., 6 pages (Dec. 2004).

* cited by examiner

END-OF-LIFE DISABLING OF A DIAGNOSTIC TEST SYSTEM

CROSS-REFERENCE TO RELATED APPLICATIONS

This application is a continuation-in-part of prior co-pending U.S. patent application Ser. No. 11/312,951, filed Dec. 19, 2005, which is incorporated herein by reference.

BACKGROUND

Patient samples often are analyzed for the presence of analytes to determine, for example, if a patient is carrying a disease, has an infection, or has been using drugs. Analytes typically are detected with immunoassay testing using antigen-antibody reactions. Conventionally, such tests have been carried out in specialized laboratories using diagnostic test systems that are large and expensive. The need for on-site examination, however, is growing rapidly. This need currently is being met by various point-of-care diagnostic test systems that can be used in a wide variety of different locations, such as hospitals, emergency rooms, health clinics, nursing homes, practitioner offices, and the homes of patients. The deployment of such point-of-care diagnostic test systems depends on the ability to keep costs below relatively low price points. In addition, point-of-care diagnostic test systems should be relatively easy to use by persons with little or no training. Ideally, such point-of-care diagnostic test systems should be capable of automatically performing diagnostic tests with minimal user input.

The relatively low price points required for the large-scale adoption of point-of-care diagnostic test systems typically results in the use of analyte testing components that are less sensitive than laboratory diagnostic test systems. What are needed are high-sensitivity point-of-care diagnostic test systems and methods that can be produced within the cost constraints that are required for large-scale adoption.

SUMMARY

In one aspect, the invention features a diagnostic test system that includes a test unit and a disabling unit. The test unit performs at least one diagnostic test on a diagnostic assay to determine whether at least one analyte is present within a sample. The disabling unit determines a measure of current lifetime of the test unit and disables the test unit in response to a determination that the current lifetime measure meets an end-of-life threshold.

In another aspect, the invention features a diagnostic test method in accordance with which at least one diagnostic test is performed on a diagnostic assay to determine whether at least one analyte is present within a sample. A measure of current lifetime of the test unit is determined. The test unit is disabled in response to a determination that the current lifetime measure meets an end-of-life threshold.

Other features and advantages of the invention will become apparent from the following description, including the drawings and the claims.

DETAILED DESCRIPTION

In the following description, like reference numbers are used to identify like elements. Furthermore, the drawings are intended to illustrate major features of exemplary embodiments in a diagrammatic manner. The drawings are not intended to depict every feature of actual embodiments nor relative dimensions of the depicted elements, and are not drawn to scale.

I. INTRODUCTION

The embodiments that are described in detail below enable high-sensitivity point-of-care diagnostic test systems and methods that can be provided within the cost constraints that are required for large-scale adoption of point-of-care diagnostic testing systems and methods. These embodiments enable point-of-care diagnostic testing applications to use testing components (e.g., semiconductor light sources, such as lasers and light emitting diodes) that are relatively low in cost yet are capable of providing high-sensitivity detection of target analytes. In particular, these embodiments leverage the lower costs that can be achieved by using optoelectronic devices with relatively short expected lifetimes (i.e., the period over which the component continues to conform to a target performance specification) to provide point-of-care diagnostic systems with high sensitivity and high accuracy. To enable the use of such testing components in point-of-care testing environments, these embodiments include a disabling unit that automatically disables the diagnostic test system upon determining that the lifetime of at least one of its testing components has expired.

II. OVERVIEW

Figure 1:
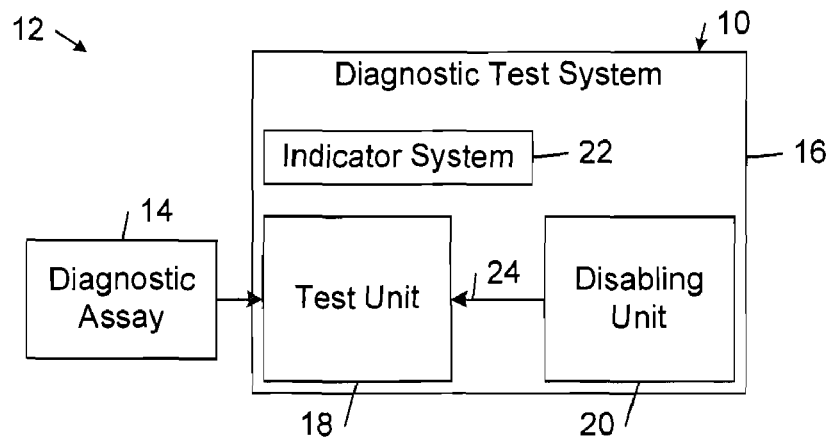
FIG. 1 is a block diagram of an embodiment of a diagnostic test system that includes a test unit and a disabling unit in an exemplary application environment.

FIG. 1 shows an embodiment of a diagnostic test system 10 in an exemplary application environment 12 that includes a diagnostic assay 14. The diagnostic test system 10 includes a housing 16, a test unit 18, a disabling unit 20, and an indicator system 22. In some embodiments, the disabling unit 20 produces a disable signal 24 in response to a determination that the lifetime of the test unit 18 has expired. The disable signal 24 triggers a disabling mechanism that disables the test unit 18.

Figure 2:
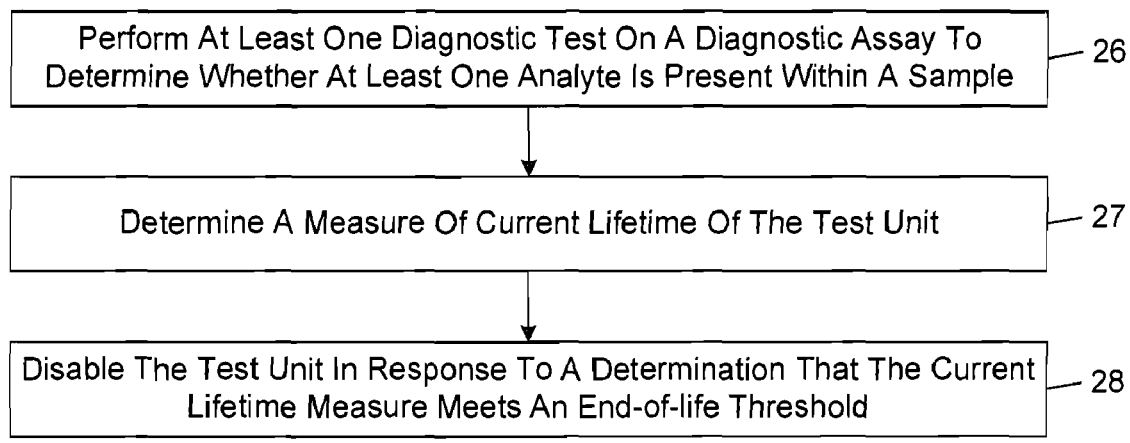
FIG. 2 is a flow diagram of an embodiment of a diagnostic test method.

FIG. 2 shows an exemplary embodiment of a diagnostic test method that is implemented by the diagnostic test system 10. In accordance with this embodiment, the test unit 18 performs at least one diagnostic test on the diagnostic assay 14 to determine whether at least one analyte is present within a sample (FIG. 2, block 26). The disabling unit 20 determines a measure of current lifetime of the test unit (FIG. 2, block 27). The disabling unit 20 disables the test unit 18 in response to a determination that the current lifetime measure meets an end-of-life threshold (FIG. 2, block 28).

In general, the diagnostic assay 14 may be any type of device for assaying a wide variety of environmental samples (e.g., toxins and chemical contaminants) and physiological samples (e.g., urine, saliva, blood, and breath). Exemplary diagnostic assays include but are not limited to lateral flow assay test strips and ELIZAs (Enzyme Linked Immuno Sorbent Assays). The diagnostic test system 10 may be configured to perform any of a wide variety of different types of diagnostic tests on the diagnostic assay 14, including tests for any type of analyte, medical or environmental condition, or substance including but not limited to hormone, a metabolite, a toxin (e.g., a biotoxins), a pathogen-derived antigen, glucose, pregnancy, infectious diseases, cholesterol, cardiac markers, drugs-of-abuse, and chemical contaminants.

The housing 16 may be made of any one of a wide variety of materials, including plastic and metal. The housing 16 protects or covers the test unit 18, the disabling unit 20, and other components of the diagnostic test system 10. The indicator system 22 may be incorporated in the housing 16 or it may be affixed to an external surface of the housing 16. In some embodiments, the housing 16 defines a receptacle that mechanically registers the diagnostic assay 14 with respect to the test unit 18.

In general, the test unit 18 includes one or more electronic components for analyzing the diagnostic assay 14 to determine the presence of at least one analyte in the sample being assayed by the diagnostic assay 14. In some embodiments, the test unit 18 includes electronic components that measure one or more electrical properties (e.g., electrical resistance) of the sample in the diagnostic assay 14. In some embodiments, the test unit 18 includes one or more optoelectronic components that measure one or more optical properties of the sample in the diagnostic assay 14.

Some embodiments leverage the lower costs that can be achieved by using optoelectronic devices with relatively short expected lifetimes to provide point-of-care diagnostic systems with high sensitivity and high accuracy. Some of these embodiments use optoelectronic testing components that are characterized by lower durability and shorter expected lifetimes than comparable devices that are designed for other application environments, such as telecommunications applications. For example, some embodiments utilize optoelectronic components that undergo little or no accelerated aging processes (e.g., so-called "burn-in" processes). Such processes typically are used to move these components to a more stable point on their respective performance-versus-age characteristic curves and thereby ensure the reliability of these components over maximal periods of time, for example, by extending the period over which age-induced output variations are expected to remain within relatively tight tolerance ranges.

The test unit 18 also typically includes a control unit that analyzes the measurements to determine the presence of at least one target analyte in the sample. In general, the control unit may be implemented in any computing or processing environment, including in digital electronic circuitry or in computer hardware, firmware, or software. In some embodiments, the control unit is a microcontroller, a microprocessor, or an ASIC. In some embodiments, the control unit is incorporated within the housing 16 of the diagnostic test system 10. In other embodiments, the control unit is located in a separate device, such as a computer, that may communicate with the diagnostic test system 10 over a wired or wireless connection.

In some implementations, computer process instructions for implementing the methods that are executed by the test unit 18, as well as the data it generates, are stored in one or more machine-readable media. Storage devices suitable for tangibly embodying these instructions and data include all forms of non-volatile memory, including, for example, semiconductor memory devices, such as EPROM, EEPROM, and flash memory devices, magnetic disks such as internal hard disks and removable hard disks, magneto-optical disks, DVD-ROM/RAM, and CD-ROM/RAM.

The disabling unit 20 is configured to disable the test unit 18 in response to a determination that the current lifetime of the test unit 18 has expired. The disabling unit 20 typically is configured to disable the test unit 18 before one or more operating characteristics of the test unit 18 are expected to fail to conform to a performance specification (or standard) that is associated with the test unit 18. For example, in some embodiments, the disabling unit 20 is configured to disable the test unit 18 before the precision, reliability, or sensitivity with which the test unit can perform one or more specified diagnostic tests falls below a specified level. In general, the disabling unit 20 may include any of a wide variety of different mechanisms for determining the current lifetime of the test unit 18. In addition, the disabling unit 20 may disable the test unit 18 in a wide variety of different ways. The diagnostic test system 10 typically is free of any reset mechanism for re-enabling the test unit 18 after it has been disabled by the disabling unit 20. In this way, a user cannot easily re-enable the test unit 18 after its designated lifetime has expired.

In general, the indicator system 22 may include any of a wide variety of different mechanisms for indicating the status of the diagnostic test system 10 or the status of a diagnostic assay test, including visual mechanisms, audio mechanisms, and vibrational mechanisms. In some implementations, the indicator system 22 includes one or more of an illumination system (e.g., one or more light-emitting diodes), an audio transducer, and a mechanical vibrator. The test unit 18 generates a status indicator control signal 22 that triggers the indicator system 22 to produce one or more non-textual sensory output signals 24 that indicate, for example, that the test unit is ready to perform a diagnostic test, that a diagnostic test is in progress, that a diagnostic test is complete (e.g., when a sufficient quantity of a labeling substance has accumulated in the control region of a lateral flow assay test strip). In some embodiments, the test unit 18 is free of any mechanism for controlling the indicator system 22 to indicate a result of a diagnostic test. This feature is particularly important for diagnostic testing applications, such as drug-of-abuse testing, where it is desirable to preserve the anonymity of persons being tested and to separate the reporting of the results from the testing location.

In some embodiments, the diagnostic test system 10 additionally includes an alphanumeric display (e.g., a two or three character light-emitting diode array) for presenting assay test results.

A power source typically supplies power to the active components of the diagnostic test system 10, including the test unit 18 and the indicator system 22. The power source may be implemented by, for example, a replaceable battery, a rechargeable battery, or a wired connection (e.g., a USB connection) to an external power source.

III. EXEMPLARY EMBODIMENTS OF THE DIAGNOSTIC TEST SYSTEM

A. A First Exemplary Embodiment of the Diagnostic Test System

Figure 3:
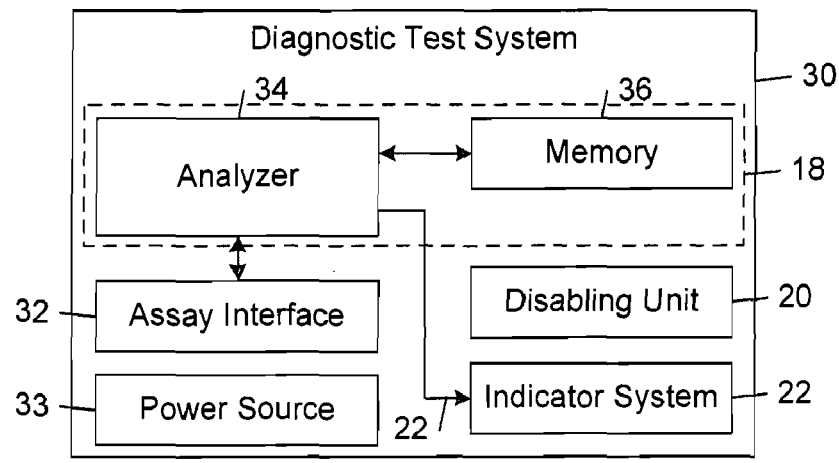
FIG. 3 is a block diagram of an embodiment of the diagnostic test system shown in FIG. 1.

FIG. 3 shows an embodiment 30 of the diagnostic test system 10 that includes an assay interface 32 and a power source 33 in addition to the test unit 18, the disabling unit 20, and the indicator system 22. In this embodiment, the test unit 18 includes an analyzer 34 and a memory 36.

In some embodiments, the assay interface 32 is implemented by a port that receives a diagnostic assay, such as a lateral flow assay test strip. In other embodiments, the assay interface 32 is implemented by a coupling mechanism that enables the diagnostic test system 30 to be brought into the proximity of diagnostic assays, such as liquid form ELIZA assays that are performed in test tubes or micro-titer plates, or other assays in which handling might interrupt the function of the assay. In some embodiments, assay interface 20 couples with a sample container that contains the diagnostic assay 14, which includes a sample to be analyzed by the analyzer 34. The diagnostic assay 14 may be, for example, a reservoir, a lateral flow assay test strip, or any other device that carries the sample.

The analyzer 34 measures one or more properties of the diagnostic assay 14 that is interfaced with the assay interface 32 and analyzes the measurements to determine whether one or more target analytes are present in the sample carried by the diagnostic assay 14. In some embodiments, the analyzer 34 includes a control unit and a measurement system that detects the assay result. The measurement system may include, for example, one or more optoelectronic detectors (e.g., one or more a photodiode, a CCD imager, and a CMOS imager). In addition to analyzing the measurements made by the measurement system, the control unit typically choreographs the operation of the diagnostic test system 30, including providing control mechanisms for timing and/or detection of start and stop times.

In some embodiments, the memory 36 stores a test program, which specifies a process that is executed by the control unit to determine one or more of the following: whether a target analyte is present in the sample; the quantity (e.g., concentration) of the target analyte is in the sample; and how the levels of the detected analyte relate to a particular ailment or condition. In general, the test program may include instructions for performing any method of analyzing a diagnostic test that depends on the presence or absence of at least one target analyte, including but not limited to any of the analytes described herein. For example, in some exemplary embodiments, the test program defines a process for optically analyzing a lateral flow assay test for a particular change in appearance (e.g., color) of a line in the assay test, wherein the change in appearance indicates the presence of a target analyte being tested for. In one embodiment in which diagnostic test system 10 executes a pregnancy test, the test program specifies a method for reviewing a lateral flow assay strip for a change of color indicating the presence of human chorionic gonadotropin (HCG) to determine whether or not a particular person is pregnant.

In general, a more precise and accurate result can be determined by using the analyzer 34 to analyze the diagnostic assay 14 as compared to manual reading of the assay. For example, in a typical pregnancy test, the degree of color change in an assay can vary greatly depending upon the level of HCG included in the blood or urine of the patient being tested. In early detection cases, the color change of the assay strip is relatively minor and may be undetectable to a user or may leave the user with questions regarding whether or not there was actually a color change in the assay strip. However, the analyzer 34 can more precisely analyze the degree of color change and determine a particular level of HCG within the assay. In this regard, a more definite and sensitive test result can be achieved.

B. A Second Exemplary Embodiment of the Diagnostic Test System

Figure 4:
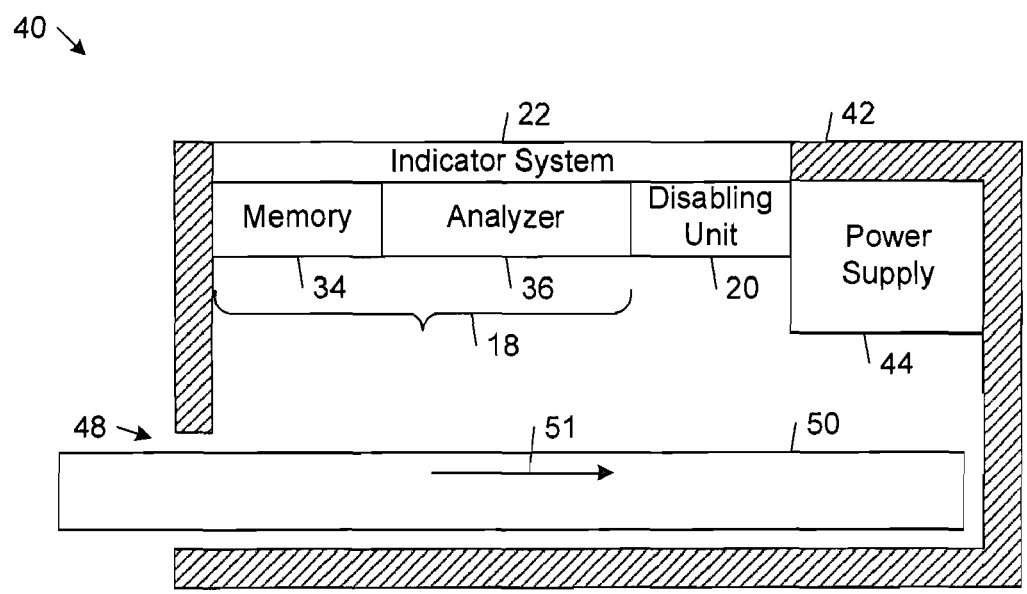
FIG. 4 is a block diagram of an embodiment of the diagnostic test system shown in FIG. 3.

FIG. 4 shows an embodiment 40 of the diagnostic test system 30 shown in FIG. 3. The diagnostic test system 40 includes a housing 42 that contains the test unit 18, the disabling unit 20, and a power supply 44. In this embodiment, the analyzer 36 includes an optoelectronic reader that includes a light source (e.g., a semiconductor laser or a semiconductor light emitting diode) and a light sensor (e.g., a semiconductor photodetector). The housing 42 includes a port 48 for receiving a test strip 50. When the test strip 50 is loaded in the port 48, the analyzer 36 obtains light intensity measurements from the test strip 50. In general, the light intensity measurements may be unfiltered or they may be filtered in terms of at least one of wavelength and polarization. The analyzer 36 computes at least one parameter from one or more of the light intensity measurements. In some implementations, the diagnostic test system 40 is fabricated from relatively inexpensive components enabling it to be used for disposable or single-use applications.

The housing 42 may be made of any one of a wide variety of materials, including plastic and metal. The housing 42 forms a protective enclosure for the memory 34, the analyzer 36, the disabling unit 20, the power supply 44, and other components of the diagnostic test system 40. The housing 42 also defines a receptacle that mechanically registers the test strip 50 with respect to the analyzer 36. The receptacle may be designed to receive any one of a wide variety of different types of test strips 50.

In general, the test strip 50 supports lateral flow of a fluid sample along a lateral flow direction 51. The test strip 50 typically includes a labeling zone containing a labeling substance that binds a label to a target analyte and a detection zone that includes at least one test region containing an immobilized substance that binds the target analyte. One or more areas of the detection zone, including at least a portion of the test region, are exposed for optical inspection by the analyzer 36. The exposed areas of the detection zone may or may not be covered by an optically transparent window.

As mentioned above, the analyzer 36 includes a reader that has one or more optoelectronic components for optically inspecting the exposed areas of the detection zone of the test strip 50. In some implementations, the analyzer 36 includes at least one light source and at least one light detector. In some implementations, the light source may include a semiconductor light-emitting diode and the light detector may include a semiconductor photodiode. Depending on the nature of the label that is used by the test strip 50, the light source may be designed to emit light within a particular wavelength range or light with a particular polarization. For example, if the label is a fluorescent label, such as a quantum dot, the light source would be designed to illuminate the exposed areas of the detection zone of the test strip 50 with light in a wavelength range that induces fluorescence from the label. Similarly, the light detector may be designed to selectively capture light from the exposed areas of the detection zone. For example, if the label is a fluorescent label, the light detector would be designed to selectively capture light within the wavelength range of the fluorescent light emitted by the label or with light of a particular polarization. On the other hand, if the label is a reflective-type label, the light detector would be designed to selectively capture light within the wavelength range of the light emitted by the light source. To these ends, the light detector may include one or more optical filters that define the wavelength ranges or polarizations axes of the captured light.

The analyzer 36 also includes a control unit that processes the light intensity measurements that are obtained by the reader. In general, the control unit may be implemented in any computing or processing environment, including in digital electronic circuitry or in computer hardware, firmware, or software. In some embodiments, the control unit includes a processor (e.g., a microcontroller, a microprocessor, or ASIC) and an analog-to-digital converter. In the illustrated embodiment, the control unit is incorporated within the housing 42 of the diagnostic test system 40. In other embodiments, the control unit is located in a separate device, such as a computer, that may communicate with the diagnostic test system 40 over a wired or wireless connection.

The power supply 44 supplies power to the active components of the diagnostic test system 40, including the memory 34, the analyzer 36, the disabling unit 20, and the indicator 22. The power supply 44 may be implemented by, for example, a replaceable battery or a rechargeable battery.

C. A Third Exemplary Embodiment of the Diagnostic Test System

Figure 5:
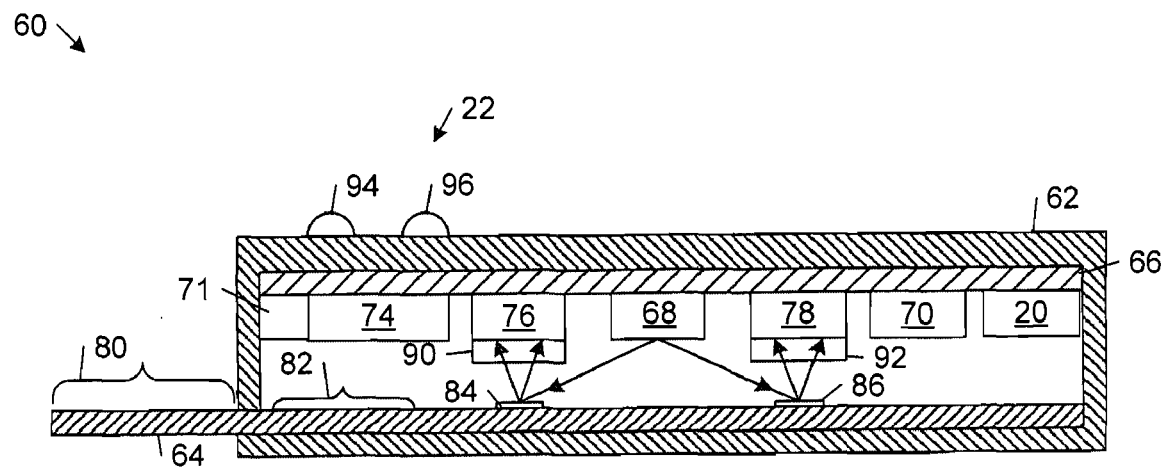
FIG. 5 is a block diagram of an embodiment of the diagnostic test system shown in FIG. 4.

FIG. 5 shows an embodiment 60 of the diagnostic test system 40 shown in FIG. 4. The diagnostic test system 60 can test for any desired medical or environmental condition or substance including but not limited to any of the analytes described herein. The diagnostic test system 60 includes a housing 62, a test strip 64, and a circuit 66 that includes a light source 68, a battery 70, a memory 71, a control unit 74, two photodetectors 76 and 78, and the disabling unit 20.

The housing 62 can be made of plastic or other material suitable for safely containing the liquid sample being analyzed. In the illustrated embodiment, housing 62 has an opening through which a portion of the test strip 64 extends for application of the sample to a sample receiving zone 80 of the test strip 64. In other embodiments, the test strip 64 is enclosed in the housing 62 during testing, and application of the sample to the test strip 64 is through an opening in the housing 62.

The test strip 64 typically is implemented by a lateral flow assay test strip. In some embodiments, the test strip 64 has a substance for labeling the target analyte that preferably includes a quantum dot or a similar structure that fluoresces at a constant intensity when exposed to light of the proper wavelength. For a test, a user applies a sample to sample receiving zone 80 of test strip 64. The sample flows from receiving zone 80 into a labeling zone 82 inside the housing 62. The labeling substance binds the quantum dot or other persistent fluorescent structure to the target analyte. The sample including the labeling substance then enters a capture or detection zone that includes a test stripe 84 and a control stripe 86. The test stripe 84 is a region containing an immobilized substance selected to bind and retain the labeled complex containing the target analyte and the quantum dot. The control stripe 86 is a region containing an immobilized substance selected to bind to and retain to the labeling substance.

The light source 68 in circuit 66 illuminates the test stripe 84 and the control stripe 86 during testing. The light source 68 typically is a light emitting diode (LED) or a laser diode that emits light of a frequency that causes fluorescence of any quantum dots in the test stripe 84 or the control stripe 86. Generally, the quantum dots fluoresce under a high frequency (or short wavelength) light (e.g., blue to ultraviolet light) and the fluorescent light has a lower frequency (or a longer wavelength) than the light from light source 68.

The photodetectors 76 and 78 are in the respective paths of light emitted from the test stripe 84 and the control stripe 86 and measure the fluorescent light from the respective stripes 84 and 86. A baffle or other light directing structure (not shown) can be used to direct light from the test stripe 84 to the photodetector 76 and light from the control strip 86 to the photodetector 78. In the embodiment of FIG. 5, the photodetectors 76 and 78 have respective color filters 90 and 92 that transmit light of the frequency associated with the selected fluorescent light but block other frequencies, especially the frequency of light emitted from light source 68. Additionally, the labeling substance can include two types of quantum dots. One of the types of quantum dots emits a first wavelength of light and is attached to a substance that binds to the target analyte and to the test stripe 76. The other type of quantum dot emits light of a second wavelength and binds to the control stripe 78. The color filters 90 and 92 can then be designed so that photodetector 76 measures fluorescent light from the type of quantum dot that the test stripe 84 traps when the target analyte is present while photodetector 78 measures fluorescent light from the type of quantum dot that the control strip 86 traps.

The quantum dots provide fluorescent light at an intensity that is consistent for long periods of time, instead of rapidly degrading in the way that the intensity of conventional test dyes degrade when exposed to light. As a result, the intensity measurements from the detectors 76 and 78, which indicate the amount of fluorescent light, are proportional to the number of quantum dots in the respective stripes 84 and 86 and are not subject to rapid changes with time. These intensity measurements thus provide a quantitative indication of the concentration of the target analyte.

The control unit 74, which can be a standard microcontroller or microprocessor with an analog-to-digital converter, receives electrical signals from the detectors 76 and 78. The electric signals indicate the measured intensities from stripes 84 and 86. The control unit 74 processes the electrical test signals and then operates an output system as required to indicate test results. In FIG. 5, for example, the output system includes LED lights 94 and 96. The control unit 74 can activate one light 94 when the fluorescent light from the test stripe 84 is above a threshold level marking the presence of the target analyte in test stripe 84. The control unit 74 can activate the other light 96 when the intensity of fluorescent light from the test stripe 84 is below the threshold level but the intensity that the photodetector 78 measures from the control stripe 86 is above a threshold level therefore indicating that the sample has passed through test stripe 84. A system with three or more LEDs or particular patterns of flashing of one or more LEDs can similarly indicate other test results (e.g., an inconclusive test) or a test status (e.g., to indicate a test in progress).

D. A Fourth Exemplary Embodiment of the Diagnostic Test System

Figure 6:
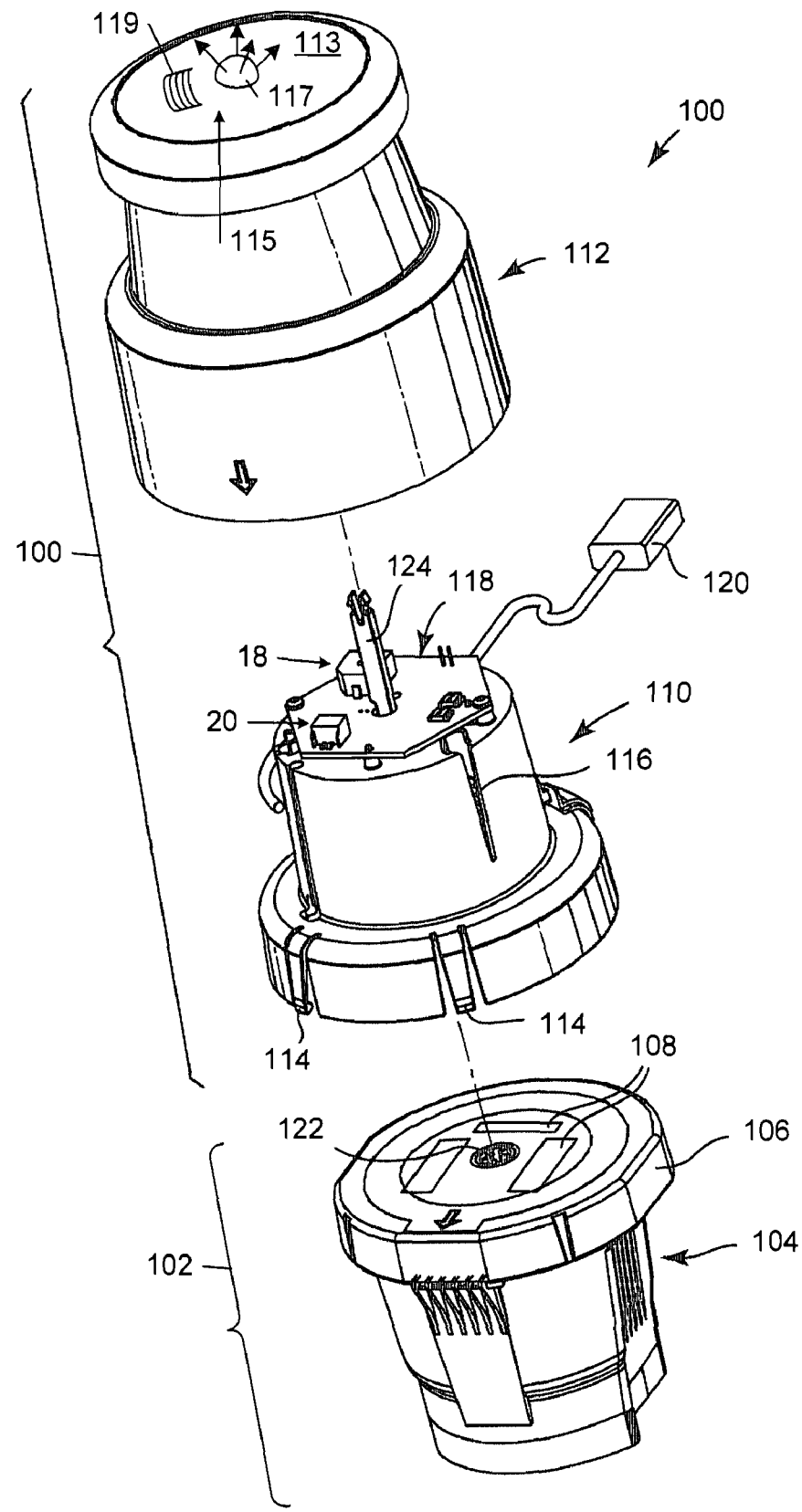
FIG. 6 is a block diagram of an embodiment of the diagnostic test system shown in FIG. 3.

FIG. 6 shows an embodiment 100 of the diagnostic test system 30 shown in FIG. 3 that is configured to analyze an embodiment 102 of the diagnostic assay 14 shown in FIG. 1.

The diagnostic assay 102 includes a sample collection cup 104 and a diagnostic lid 106. The sample collection cup 104 is configured to receive test fluids (e.g., urine and blood) from a patient. The lid 106 is configured to interface with an open end of the cup 104 and substantially enclose the sample fluid within the cup 104. In the illustrated embodiment, the lid 106 is substantially transparent to light produced by the test unit 18. The lid 106 includes a plurality of lateral flow assay strips 108 that are generally visible through lid 106.

The diagnostic test system 100 interfaces with the lid 106 of the sample collection cup 104. The diagnostic test system is formed of two parts: an inner housing 110 and an outer housing 112. The outer housing 112 is configured to coaxially receive the inner housing 110. The outer housing 112 includes a top surface 113 that supports an embodiment 115 of the indicator system 22 (see FIG. 1) that includes a single light emitting diode 117 and an audio transducer 119. Circuitry 118 of the inner housing 110 is mounted to a top surface of the inner housing 110. The circuitry 118 includes the test unit 18 and the disabling unit 20. The test unit 18 includes an optoelectronic camera (not shown) that is positioned within inner housing 110. The camera allows the diagnostic test system 100 to optically analyze the assay strips 108 in the lid 106. The inner housing 110 also includes a connector 120 that enables the control unit to communicate with a remote computer processing unit or other device. In one embodiment, the connector 120 is a universal serial bus (USB) connector.

The test unit 18 also includes a control unit (not shown). In addition to analyzing the images that are captured by the camera, the control unit 46 produces status indicator control signals that trigger the light emitting diode 117 and the audio transducer 119 to respectively produce visual and audio output signals indicating the status of a test. In some exemplary embodiments, the status indicator control signal directs the light emitting diode 117 to produce respective patterns of light flashes indicating that the diagnostic test system 100 is ready to perform a test, a diagnostic test is in progress, and a diagnostic test is complete. In some of these embodiments, the light emitting diode 117 produces a constant (non-flashing) light to indicate that the diagnostic test system 100 is ready to perform a test, a slowly flashing light to indicate that the diagnostic test system 100 is currently performing a test, and a rapidly flashing light to indicate that the diagnostic test system 100 has complete a test. In some exemplary embodiments, the status indicator control signal directs the audio transducer 119 to produce respective patterns of sound (e.g., beeps or tones) to indicate that the diagnostic test system 100 is ready to perform a test, a diagnostic test is in progress, and a diagnostic test is complete. The non-textual sensory output signals produced by the light emitting diode 117 and the audio transducer 119 may be redundant or complementary.

The diagnostic test system 100 is configured to be aligned with and pushed down and at least partially over lid 106 to secure the diagnostic test system 100 to the lid 106. Upon coupling of the diagnostic test system 100 with the lid 106, the camera that is included in the circuitry 118 is positioned to optically capture images of the assay strips 108 through the lid 106. The inner housing 110 includes tabs 114 that are circumferentially spaced around an open periphery of the inner housing 110. The tabs 114 are bent toward the lid 106 during use to grasp the lid 106 and lock the diagnostic test system 100 to the lid 106. In one embodiment, bending or unbending of the tabs 114 may indicate to the diagnostic test system 100 that a test has been performed. In one example, springs 116 interact with the inner and outer housings 110 and 112 and facilitate decoupling of the diagnostic test system 100 with the lid 106.

In the illustrated embodiment, the lid 106 includes a cavity 122 that has an aliquot plunger, and the diagnostic test system 100 includes an index member 124. After the inner housing 110 is positioned on the lid 106, the outer housing 112 is pushed toward the inner housing 110, thereby, moving the index member 124 down into the cavity 122. The index member 124 interacts with the aliquot plunger causing sample fluid in the cup 104 to be aliquot to the assays 108.

In operation, once the inner housing 110 grasps the lid 106, the timer begins a countdown of the predetermined time period required to complete the analysis of the assay strips 108 in the lid 106. The optoelectronic camera in the inner housing 110 views the assays 108 through the transparent lid 106 to determine whether or not a particular analyte is present by analyzing any color change of the test trip 108. At the end of the predetermined time period, if no analyte is detected, then the test is negative. Regardless of whether or not the analyte was detected, the test typically is complete upon the expiration of the predetermined time period. Therefore, in one embodiment, the expiration of the time period serves as an end-of-test trigger.

IV. EXEMPLARY EMBODIMENTS OF THE INDICATOR SYSTEM

As explained above, the disabling unit 20 is configured to disable the test unit 18 in response to a determination that the current lifetime of the test unit 18 has expired. The disabling unit 20 typically is configured to disable the test unit 18 before one or more operating characteristics of the test unit 18 are expected to fail to conform to a specification or standard that is associated with the test unit 18. For example, in some embodiments, the disabling unit 20 is configured to disable the test unit 18 before the precision, reliability, or sensitivity with which the test unit can perform one or more specified diagnostic tests falls below a specified level. In this regard, the disabling unit disables the test unit 18 in response to a determination that the current lifetime measure meets (e.g., is greater than or is at least equal to) an end-of-life threshold.

In some embodiments, the end-of-life threshold is a threshold value for the lifetime of the test unit 18 before which the test unit is expected to be able to perform reliably and with a particular sensitivity level, where the lifetime of the test unit 18 is measured as a continuous period or an aggregation of discrete operational (i.e., in-use) periods or a combination of both continuous and aggregated periods.

The end-of-life threshold may be selected with any factor of safety desired such that the test unit 18 is disabled prior to a target statistical probability of either electrical or mechanical degradation that decreases the sensitivity of the test unit 18 below a target level. In some embodiments, the end-of-life threshold is determined via calculations and/or experimentation in which a number of test units 18 are tested during storage periods and periods of repeated use. The lifetime values at which a specified fraction of one or more components of the test unit 18 begin to fail or the sensitivity levels of the test unit 18 fall below a desired level are determined. The end-of-life threshold typically is a lifetime value that is significantly lower than the lifetime that is determined to cause degradation or an undesired decrease in the sensitivity or reliability of the test unit 18. The desired level of sensitivity typically varies depending upon the test being run with test unit 18. For example, pregnancy tests may require less sensitivity or may allow higher error rates than a test for an infectious disease where test errors may have a more detrimental effect on the patient or others.

In one embodiment, the end-of-life threshold is selected based upon a mean time to failure (MTTF) lifetime value. The MTTF lifetime value occurs when half the units will give incorrect test results when their current lifetimes reach the MTTF lifetime. The end-of-life threshold may be adjusted or decreased to achieve a target error rate for a particular type of test. The target error rates may be based on such factors as confidence levels and economic factors.

In general, the disabling unit 20 may include any of a wide variety of different mechanisms for determining the current lifetime of the test unit 18. In some embodiments, the disabling unit 20 includes a disabling unit processing module that determines a measure of the current lifetime of the test unit 18 and produces the disable signal 24, which triggers a disabling mechanism that disables the test unit 18. In general, the disabling unit processing module may be implemented in any computing or processing environment, including in digital electronic circuitry or in computer hardware, firmware, or software. In some embodiments, the disabling unit processing module is a microcontroller, a microprocessor, or an ASIC. In some embodiments, the disabling unit processing module is incorporated within the housing 16 of the diagnostic test system 10. In other embodiments, the disabling unit processing module is located in a separate device, such as a computer, that may communicate with the diagnostic test system 10 over a wired or wireless connection.

Some embodiments of the disabling unit 20 measure the current lifetime of the test unit 18 as the difference between a measure of the current time and a fixed preset reference time. In some of these embodiments, the reference time corresponds to a fixed preset timestamp is stored in a non-volatile memory of the disabling unit 20 during manufacture of the diagnostic test system 10. The fixed preset timestamp may correspond to a current time during a particular phase of the process that is used to manufacture or assemble the diagnostic test system before shipping to a distributor or end-user. The current time may be specified in accordance with a standard reference time, such as the coordinated universal time (also referred to as "Greenwich Mean Time" or "world time") or the international atomic time (TAI), or a relative time that is maintained by a timer (e.g., a count-up timer or clock, or a count-down timer or clock). After the diagnostic test system 10 has shipped, the disabling unit 20 may determine the current lifetime of the test unit 18 by comparing a timestamp or other clock signal that is obtained from an internal or external timing mechanism to the fixed preset timestamp. For example, in some embodiments, the disabling unit 20 determines the current lifetime through an onboard, sealed clock chip that is powered by a dedicated battery and set to a reference time (e.g., 0) at a late production stage just prior to shipping. In some embodiments, the disabling unit 20 determines the current lifetime through a connection to an external host system, such as a host computer.

Figure 7:
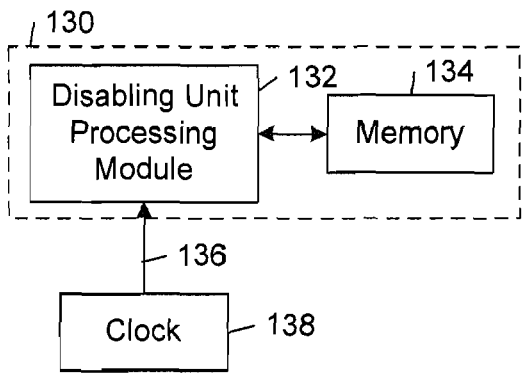
FIG. 7 is a block diagram of an embodiment of a disabling unit coupled to a clock.

FIG. 7 shows an embodiment 130 of the disabling unit 20 that includes a disabling unit processing module 132 and a memory 134. In this embodiment, the disabling unit processing module 132 receives a clock signal 136 from an internal clock 138 that is contained within the housing 16 of the diagnostic test system 10. The clock signal 136 carries an indication of the current time in terms of a standard reference time, such as the coordinated universal time (also referred to as "Greenwich Mean Time" or "world time") or the international atomic time (TAI), or a time that is measured in relation to the fixed preset reference time, which typically is stored in the memory 134.

Figure 8:
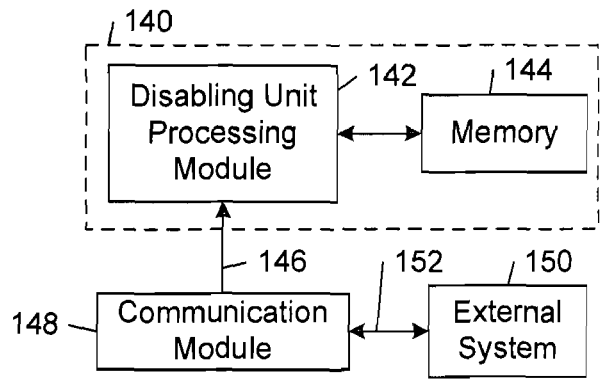
FIG. 8 is a block diagram of an embodiment of a disabling unit coupled to a communication module that communicates with an external system.

FIG. 8 shows an embodiment 140 of the disabling unit 20 that includes a disabling unit processing module 142 and a memory 144. In this embodiment, the disabling unit processing module 142 receivers a timestamp signal 146 from an internal communication module 148, which is contained within the housing 16 of the diagnostic test system 10. The timestamp signal 146 typically carries an indication of the current time in terms of a standard reference time, such as the coordinated universal time (also referred to as "Greenwich Mean Time" or "world time") or the international atomic time (TAI). The communication module 148 communicates with an external system 150 over a wired or wireless connection. The disabling unit processing module 142 is operable to query the external system 150 for the current time via the communication module 148. In response to such a query, the external system 150 transmits a signal 152 carrying an indication of the current time. The external system 150 may be, for example, a local host device that is separate from the diagnostic test system 10 or a remote host device that communicates with the communication module 148 over a network connection.

Some embodiments of the disabling unit 20 measure the current lifetime of the test unit 18 as the aggregation of each operational period during which the test unit 18 is performing at least one respective diagnostic test. In some of these embodiments, the disabling unit 20 includes a timer that measures each operational period during which the test unit 18 is performing at least one respective diagnostic test. The disabling unit 20 determines the current lifetime of the test unit 18 by aggregating the times measured by the timer. In some embodiments, the timer measures the operational periods in response to timing triggers that are correlated with a beginning and an ending of each performance of at least one respective diagnostic test by the test unit 18. The timing triggers can be any trigger for determining the beginning and ending of a diagnostic test. The timing triggers typically are activated automatically during the performance of a diagnostic test; these timing triggers typically do not require a separate action by the user to activate. In some embodiments, the timer is started in response to the detection that an assay has been loaded into test unit 18, and the timer is stopped in response to a determination that the assay has been removed from the test unit 18 or that a preset test period has passed. The timing trigger may start or stop the timer in response to one or more of the following detection mechanisms: the sensing a physical movement of the assay into or out of assay interface 32; the optical and/or electronic sensing of the introduction of a sample fluid to the assay strip or assay interface 32; the detection a color change or other indicator of the assay strip; and the detection of any other suitable action or occurrence indicating that a test has begun or has been completed. In some embodiments, the diagnostic test system 10 includes a button that allows the user to manually trigger the timer.

The disabling unit 20 may disable the test unit 18 in a wide variety of different ways.

Figure 9:
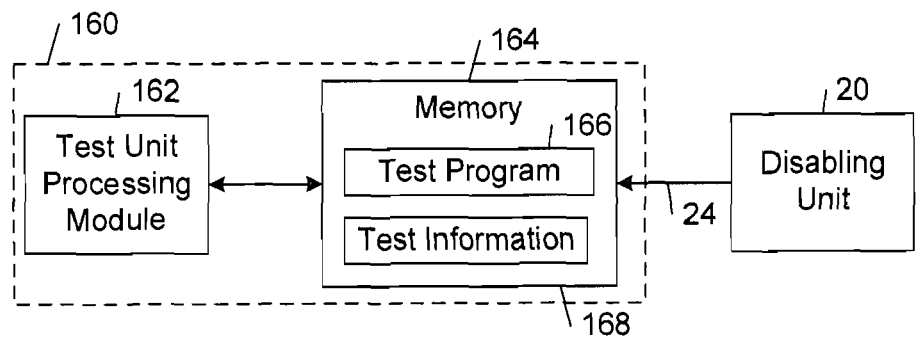
FIG. 9 is a block diagram of an embodiment of a test unit coupled to an embodiment of the disabling unit shown in FIG. 1.

FIG. 9 shows an embodiment 160 of the test unit 18 that includes a test unit processing module 162 and a memory 164. The memory 164 stores a test program 166 and test information 168. The test program 166 corresponds to a test software program or a test firmware program that is executed by the test unit processing module 162 in order to perform one or more diagnostic tests on the diagnostic assay 14. The test information 168 includes information (e.g., initialization data or parameter values) that is used by the test unit 160 to perform one or more diagnostic tests on the diagnostic assay 14. In some implementations of this embodiment, the disabling unit 20 disables the test unit 160 by erasing or otherwise disabling at least a critical portion of the test program 166 that is needed by the test unit 160 to perform one or more diagnostic tests on the diagnostic assay 14. In other implementations of this embodiment, the disabling unit 20 disables the test unit 160 by deleting at least a critical portion of the test information 168 that is needed by the test unit 160 to perform one or more diagnostic tests on the diagnostic assay 14.

Figure 10:
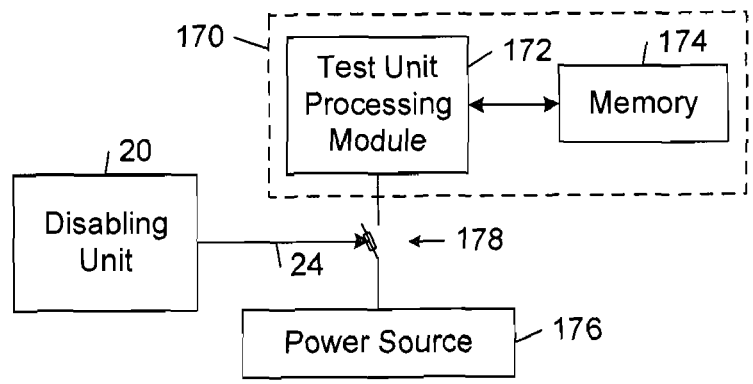
FIG. 10 is a block diagram of an embodiment of a test unit coupled to an embodiment of the disabling unit shown in FIG. 1 that selectively disconnects the test unit from a power source.

FIG. 10 shows an embodiment 170 of the test unit 18 that includes a test unit processing module 172 and a memory 174. In response to a determination that the current lifetime of the test unit 18 has expired, the disabling unit 20 disables the test unit 170 by disconnecting the test unit 18 from a power source 176 (e.g., an internal or external power supply). In this embodiment, the disabling unit 20 triggers a decoupling mechanism 178 (e.g., a fuse or a switch) that breaks the electrical connection between the test unit 170 and the power source 176 in response to the disable signal 24 that is produced by the disabling unit 20.

In some embodiments, in response to a determination that the current lifetime of the test unit 18 has expired, the disabling unit 20 is configured to burn a fuse or activate some other permanent decoupling mechanism within test unit 18 in order to prevent use of test unit 18 to diagnostically access an assay received by assay interface 20. The decoupling mechanism may be configured to: deprive the test unit 18 of power; disrupt communication between the assay interface 32 and the test unit processing module 172; and/or disrupt communication between test unit processing module 172 and the memory 174.

The embodiments of the disabling unit 20 described herein are configured to prevent use of the diagnostic test system 10 after determining that the lifetime of the test unit 18 has expired. Therefore, even if a particular patient or caregiver believes that a particular diagnostic test system is reliable, the patient or caregiver cannot continue to use the diagnostic test system 10. This feature of the disabling unit 20 is desirable because any subsequently performed tests are expected to have an increased chance of error or decreased sensitivity. Prevention of use for more than the designated lifetime is particularly important in practice areas where users do not generally believe that diagnostic test systems are disposable. In particular, in more complicated diagnostic tests, the diagnostic test systems are generally believed by healthcare workers and others to be expensive pieces of equipment that are not generally disposable. As such, healthcare workers or other individuals having this belief may not be comfortable with disposing of a diagnostic test system that still appears to be working properly. In these application environments, the disabling unit 14 protects against undesired or unreliable uses of the diagnostic test system 10. Furthermore, use of the disabling unit 20 allows inexpensive parts to be used in the diagnostic test system 10 without a worry that such parts will be used beyond the point when they can provide reliable and sensitive test results.

V. CONCLUSION

The embodiments that are described in detail herein enable high-sensitivity point-of-care diagnostic test systems and methods that can be provided within the cost constraints that are required for large-scale adoption of point-of-care diagnostic testing systems and methods. These embodiments enable point-of-care diagnostic testing applications to use testing components (e.g., semiconductor light sources, such as lasers and light emitting diodes) that are relatively low in cost yet are capable of providing high-sensitivity detection of target analytes. In particular, these embodiments leverage the lower costs that can be achieved by using optoelectronic devices with relatively short expected lifetimes (i.e., the period over which the component continues to conform to a target performance specification) to provide point-of-care diagnostic systems with high sensitivity and high accuracy. To enable the use of such testing components in point-of-care testing environments, these embodiments include a disabling unit that automatically disabling the diagnostic test system upon determining that the lifetime of at least one of its testing components has expired.

Other embodiments are within the scope of the claims.

What is claimed is:

1. A diagnostic test system, comprising:
    a test unit operable to perform at least one diagnostic test on a diagnostic assay to determine whether at least one analyte is present within a sample; and
    a disabling unit operable to determine a measure of current lifetime of the test unit and to permanently disable the test unit in response to a determination that the current lifetime measure meets an end-of-life threshold.

2. The diagnostic test system of claim 1, wherein the disabling unit determines the current lifetime measure from a difference between a timestamp specifying current time and a fixed preset timestamp.

3. The diagnostic test system of claim 1, wherein the disabling unit determines the current lifetime measure from an aggregation of each operational period during which the test unit is performing at least one respective diagnostic test.

4. The diagnostic test system of claim 3, wherein the disabling unit measures each of the operational periods in response to triggers correlated with a beginning and an ending of each performance of at least one respective diagnostic test by the test unit.

5. The diagnostic test system of claim 1, further comprising a clock that produces a clock signal indicative of current time, wherein the disabling unit is operable to determine the current lifetime measure based on the clock signal.

6. The diagnostic test system of claim 1, further comprising a communication module operable to communicate with an external system, wherein the disabling unit is operable to determine the current lifetime measure based on a current timestamp received from the external system via the communication module.

7. The diagnostic test system of claim 1, further comprising a power source connected to the test unit, wherein the disabling unit is operable to electrically disconnect the test unit from the power source in response to the determination that the current lifetime measure meets the end-of-life threshold.

8. The diagnostic test system of claim 1, wherein the test unit comprises a machine-readable memory storing information enabling the test unit to determine whether the at least one analyte is present within the sample, and the disabling unit is operable to delete at least a portion of the information from the memory in response to the determination that the current lifetime measure meets the end-of-life threshold.

9. The diagnostic test system of claim 8, wherein the memory stores machine-readable instructions that are executed by the test unit in order to determine whether the at least one analyte is present within the sample, and the disabling unit is operable to delete at least a portion of the instructions from the memory in response to the determination that the current lifetime measure meets the end-of-life threshold.

10. The diagnostic test system of claim 1, wherein the diagnostic test system is free of any reset mechanism for re-enabling the test unit after the test unit has been disabled by the disabling unit.

11. A diagnostic test system, comprising:
    test unit means for performing at least one diagnostic test on a diagnostic assay to determine whether at least one analyte is present within a sample; and
    disabling unit means for determining a measure of current lifetime of the test unit and permanently disable the test unit in response to a determination that the current lifetime measure meets an end-of-life threshold.

12. A diagnostic test method, comprising:
performing at least one diagnostic test on a diagnostic assay to determine whether at least one analyte is present within a sample;
determining a measure of current lifetime of the test unit; and
permanently disabling the test unit in response to a determination that the current lifetime measure meets an end-of-life threshold.

13. The diagnostic test method of claim 12, wherein the determining comprises determining the current lifetime measure from a difference between a timestamp specifying current time and a fixed preset timestamp.

14. The diagnostic test method of claim 12, wherein the determining comprises determining the current lifetime measure from an aggregation of each operational period during which the test unit is performing at least one respective diagnostic test.

15. The diagnostic test method of claim 14, further comprising measuring each of the operational periods in response to triggers correlated with a beginning and an ending of each performance of at least one respective diagnostic test.

16. The diagnostic test method of claim 12, further comprising producing a clock signal indicative of current time, wherein the determining comprises determining the current lifetime measure based on the clock signal.

17. The diagnostic test method of claim 12, further comprising receiving a current timestamp from an external system, wherein the determining comprises determining the current lifetime measure based on the current timestamp received from the external system.

18. The diagnostic test method of claim 12, wherein the disabling comprises electrically disconnecting the test unit from a power source in response to the determination that the current lifetime measure meets the end-of-life threshold.

19. The diagnostic test method of claim 12, further comprising storing information enabling the determination of whether the at least one analyte is present within the sample in a machine-readable memory, and the disabling comprises deleting at least a portion of the information from the memory in response to the determination that the current lifetime measure meets the end-of-life threshold.

20. The diagnostic test method of claim 19, wherein the storing comprises storing machine-readable instructions that are executed in order to determine whether the at least one analyte is present within the sample, and the disabling comprises deleting at least a portion of the instructions from the memory in response to the determination that the current lifetime measure meets the end-of-life threshold.

* * * * *